United States Patent
Red'kina

[11] Patent Number: 5,951,978
[45] Date of Patent: Sep. 14, 1999

[54] MICROORGANISMS FOR IMPROVING PLANT PRODUCTIVITY

[75] Inventor: Tatiana Vasilienva Red'kina, Moscow, U.S.S.R.

[73] Assignee: Tatko Biotech, Inc., Peoria, Ill.

[21] Appl. No.: 09/210,403

[22] Filed: Dec. 11, 1998

Related U.S. Application Data

[60] Provisional application No. 60/111,776, Dec. 10, 1998.

[51] Int. Cl.$^6$ .............................. C12N 1/20; A61K 38/44; A61K 38/54
[52] U.S. Cl. .......................... 424/93.3; 424/93.4; 47/58; 435/252.4
[58] Field of Search .................... 435/252.4; 47/57.6, 47/58; 71/6, 7; 424/93.4, 93.47, 93.48, 93.3

[56] References Cited

U.S. PATENT DOCUMENTS

| | | | |
|---|---|---|---|
| 5,147,441 | 9/1992 | Megeed | 435/252.4 |
| 5,697,186 | 12/1997 | Neyra et al. | 47/57.6 |

OTHER PUBLICATIONS

Bashan et al., "Enhanced Growth of Wheat and Soybean Plants Inoculated with Azopirillum Brasilense Is Not Necessarily Due to General Enhancement of Mineral Uptake," Appl. Environ. Microbiol., vol. 56, No. 3, pp. 769–755 (1990).

O'Hara et al., "Effect of Inoculation of Zea Mays with Azopirillum Brasilense Strains Under Temperate Conditions," Can. J. Microbiol., vol. 27, pp. 871–877 (1981).

Okon et al., "Agronomic Applications of Azospirillum: An Evaluation of 20 Year Worldwide field Inoculation," Soil Biol. Biochem., vol. 26, No. 12, pp. 1591–1601 (1994).

Smith et al., "Responses of Sorghum and Pennisetum species to the $N_2$–Fixing Bacterium Azospirillum Brasilense," Appl. Environ. Microbiol., vol. 47, No. 6, pp. 1331–1336 (1984).

Okon et al., "Root–Associated Azospirillum Species Can Stimulate Plant Growth," ASM NEWS, vol. 63, No. 7, p. 366.

*Primary Examiner*—Herbert J. Lilling
*Attorney, Agent, or Firm*—Fitch, Even, Tabin & Flannery

[57] ABSTRACT

The present invention is directed to a crop inoculant that includes *Azospirillum brasilense* SAB MKB. The crop inoculant is effective for consistently improving soil quality and increasing plant productivity over a wide range of soil types and climate conditions, and wide range of plant types.

16 Claims, No Drawings

MICROORGANISMS FOR IMPROVING PLANT PRODUCTIVITY

This application claims the benefit of U.S. Provisional application No. 60/111,776, filed Dec. 10, 1998.

The present invention relates to microorganisms which are effective for improving plant productivity. More particularly, the invention provides a crop inoculant that includes *Azospirillum brasilense* SAB MKB which is effective for significantly and consistently improving plant productivity of non-legume, legumes and vegetable crops over a wide range of soil and climate conditions.

BACKGROUND OF THE INVENTION

A number of microorganisms are known to have beneficial effects on plant growth. Among these are nitrogen fixing bacteria of the Rhizobium species, which are symbionts of leguminous species. Azospirillum species, which are free living nitrogen fixing bacteria associated with the roots of grasses, are also now recognized for their plant growth promoting qualities (Mishustin and Shilnikova, Moscow, Science Publ. House, 1973; Mishustin and Shilnikova, Moscow, Science Publ. House, 1968). More specifically, certain strains of *Azospirillum brasilense* have been shown to enhance accumulation of various minerals in wheat and soybean (Bashan et al., Applied and Environ. Microbiol., 56(3):769–775 (1990)), increase dry weights of maize shoots (O'Hara et al., Can. J. Microbiol., 27:871–877 (1981), and increase dry weights of sorghum, pearl millet and napier grass (Smith et al., Applied and Environ. Microbiol., 47(6):1331–1336 (1984)).

Inoculation of seeds or soil with beneficial microorganisms, including Azospirillum, for crop improvement has been practiced for a number of years. However, variable and inconsistent results have often been observed possibly due to loss of inoculant viability or variability of dosage due to changes in inoculant viability (Okon et al., CRC Crit. Rev. Biotechnology, 6:61–85 (1987)). Further, the use of specific types of microorganisms as crop inoculants has met with varying degrees of success most likely due to variables that include: (1) the presence or absence of adequate micro- and macro-nutrients in the soil to support the propagation of the microorganisms; (2) the amount of organic material in the soil available to hold nutrient and microbes in the soil and provide a suitable environment for microbial growth; (3) the presence or absence of certain minerals or compounds required by the plant for proper uptake of the nutrients provided by microbial activity; and (4) variations in soil characteristics such as soil type, pH, temperature and moisture.

A number of Azospirillum strains have been isolated from southern areas. These strains seem to have limited adaptive capabilities when introduced into other soil types in different climate zones (Bashan et al., Can. J. Microbiol., 36:591–608 (1990); Nur et al., Can. J. Microbiol., 26(4):482–485 (1980); Smith et al., Applied and Environ. Microbiol., 47(6):1331–1336 (1984); O'Hara et al., Can. J. Microbiol., 27:871–877 (1981)). Further, these types of microorganisms were not very effective simulators of legume-rhizobia symbiosis as they tended to stimulate the growth of plant dry weight and nodule formation, but did not always provide an increase in nitrogenase activity (Bashan et al., Applied and Environ. Microbiol., 56(3):769–775 (1990); Yahalom et al., Applied and Environ. Microbiol., 33(6):510–519 (1987); Schmidt et al., Azospirillum IV: Genetics, Physiology, Ecology, Springer-Verlag, pp. 92–101, (1988)).

SUMMARY OF THE INVENTION

The present invention is directed to a microbial inoculant that is effective for increasing plant productivity and soil quality. In an important aspect of the invention, the microbial inoculant includes the microorganism *Azospirillum brasilense* SAB MKB (referred to herein as "MKB"). The use of MKB as a microbial inoculant is effective for increasing the productivity of both nonlegume and legume plants as well as vegetable plants over a wide variety of soil types and climates One important aspect of the invention is directed to biologically pure cultures of MKB having accession number NRRL B-30082 (marked strain) and NRRL B-30081 (unmarked strain). MKB may be used as a microbial inoculant either alone or in combination with other agronomically beneficial microorganisms. Application of the microbial inoculant to the plant or the soil provides an increased level of soil nitrogen, improves mineral uptake into plants, stimulates plant growth through the production of plant growth regulators, and inhibits phytopathogenic microflora.

In another important aspect, the present invention provides a method for growing MKB. In accordance with the method of the invention, MKB is inoculated into a legume extract medium and cells are growth under conditions effective for providing a cell density of about $10^8$ to about $10^9$ cells/ml.

DETAILED DESCRIPTION OF THE INVENTION

Definitions

The term "plant productivity" or "crop productivity" refers generally to any aspect of growth or development of a plant that is a reason for which the plant is grown. For example, when referring to food crops, such as grains or vegetables, crop productivity generally refers to the yield of grain or fruit, etc., harvested from a particular crop. However, for "crops" such as turf grass, plant productivity may refer to growth rate, turf density, disease resistance and the like. Thus, for purposes of the present invention, improved plant or crop productivity refers broadly to improvements in yield of grain, fruit, flowers, or other plant parts harvested for various purposes, improvements in growth of plant parts, including stems, leaves and roots, improved resistance to disease, improved survivability in extreme climate, and similar improvements of the growth and development of plants. Examples of agronomically beneficial microorganisms include Bacillus, Pseudomonas, Rhizobia, phototrophic and cellulose degrading bacteria, Clostridium, Trichoderma and the like.

"Improving soil quality" refers to increasing nitrogen levels in the soil and reducing the number of phytotoxic microorganisms.

As used herein "microbial inoculant" or "inoculum" refers to a preparation that includes *Azospirillum brasilense* SAB MKB. *Azospirillum brasilense* SAB MKB refers to both the marked strain, i.e. having streptomycin resistance, having accession number NRRL B-30082; and unmarked strain, i.e. no streptomycin resistance, having accession number NRRL B-30081. (Both strains were deposited in the Agricultural Research Service Culture Collection (NRRL), USDA, Peoria, Ill. on Dec. 9, 1998).

As used herein "biologically pure" refers to a microbial inoculant were MKB is the only agronomically beneficial strain added to the inoculum. The microbial inoculant may include other microorganisms that do not provide any agronomic benefit.

As used herein an "agronomically beneficial strain" refers to microorganisms that are effective for increasing plant productivity. Microorganisms that provide agronomic benefit in addition to SAB include symbiotic and nonsymbiotic microorganisms which may be effective for making nutrients more bioavailable to plants, and microorganisms that inhibit phytopathogenic microflora and stimulate plant growth.

Isolation of Organism

In this aspect of the invention, MKB was isolated from turfty-podzolic soil during March in northern areas of the European part of Russia. This type of soil is representative of a poor northern climate soil having low nutrient levels. While not intending to be bound by any theory, it is thought that MKB is better able to survive under poor soil conditions, and hence adapt to a wide variety of soil conditions, because it was initially isolated from a poor soil.

Soil samples were enriched using standard techniques by culture in medium containing about 1% sodium lactate and about 0.1% yeast extract. Pure cultures of MKB were isolated by passage of enriched preparations on solid agar-like media, such as for example, potato agar, beef extract, complex media A, and complex media D (both described in the examples), with the addition of ammonium sulfate. The presence of MKB was confirmed by observing culture preparations under a phase contrast microscope. In an important aspect of the invention, MKB has the following morphological, physiological and biochemical characteristics.

Staining characteristics: gram negative

Cell size: about 0.5 to 0.6 microns in diameter and about 1 to 1.5 microns in length, slightly curved.

Morphology: MKB morphology is dependent on the type of medium used for culturing. Vibrioid forms occur on solid and semisolid media and S-shapes occur in liquid culture. Growth on potato agar results in the formation of large, opaque, round, slimy pink colored colonies with a metallic luster. Growth on beef extract agar results in the formation of small round colonies which are round, opaque and white in color. Growth on medium A provides large colonies of a deep pink color, dry border (edge), and slimy in the center. In an important aspect of the invention, MKB produces a pink carotenoid pigment, rodovibrin.

Motility: Movement is typically wavy and rotatory, and motility is provided by a single polar flagellum in liquid medium and by numerous lateral flagellum on solid medium. In an important aspect of the invention, the presence of flagellum provides MKB with a improved moving capacity and allows MKB applied as an inoculum to quickly reach the root systems of the plants.

Cyst formation: MKB initially forms cysts and involution forms (spheroplasts) when cultured for about 10 to 14 days on an enriched media such as potato agar, beef extract, or Medium A. After multiple passages on enriched media, the ability to form spheroplasts is lost, and spheroplast formation does not occur even where MKB is cultured on a poor media (for example, water with 0.5% calcium lactate).

Growth of MKB

In an important aspect of the invention, MKB can be maintained and grown in a manner which is effective for maintaining the stability and consistency of the strain. Even with repeated subculturing, MKB is stable in that the ability of MKB to fix nitrogen, produce plant growth regulators, and inhibit phytotoxic organisms does not decrease from its initial levels.

MKB can be grown and stably maintained on minimal mediums that include a salt of an organic acid and various macro and micronutrients. In an important aspect of the invention, MKB can be propagated with minimal mediums (such as water with about 0.5% Ca-lactate) and still maintain its ability to fix nitrogen.

In another aspect of the invention, MKB can tolerate or even grow under a wide variety of environmental conditions. MKB does not require additional growth factors, is chemoorganotrophic, and does not have fermentative ability.

In another aspect of the invention, MKB can grow under anaerobic conditions. Under anaerobic conditions, MKB utilizes $NO_3$ as an terminal electron acceptor, ultimately resulting in the conversion of $NO_3$ to $N_2$.

In another important aspect of the invention, MKB can be easily grown on an industrial scale. This industrial scale method of culturing MKB is effective for providing a high rate of biomass per unit volume and provides a crop inoculum that is more tolerable to storage conditions.

In this aspect of the invention, MKB is inoculated into a legume extract medium. The medium includes a water extract of legumes (seeds and/or stems, but not roots) along with a salt of an organic acid and added nitrogen. Appropriate salts of organic acids include calcium or sodium salts of malate, succinate, lactate, butyrate, propionate, ethanol, and mixtures thereof. The optimal sources of carbon for growth of nitrogen fixing microorganisms include sodium malate, sodium succinate, sodium lactate, and ethanol. Nitrogen sources useful for growing MKB include ammonium salts, nitrate salts, peptone, yeast lysate, mixtures of nitrogen containing amino acids, and mixtures thereof.

The inoculated legume extract medium is then cultured at a time, temperature and aeration rate effective for providing a cell density having an optical density of at least about 3.0. In an important aspect of the invention, culture time will typically range from about 24 to about 48 hours, temperatures are maintained at about ambient temperature, and standard aeration rates are used such that $O_2$ levels are not limiting.

Application of MKB

MKB may be applied by methods known in the art which include seed coating, applications with peat or planting materials, and entrapment in biopolymers. In the aspect of the invention where seed coating is utilized, coating may be effected by methods described and referred to in Brown, Seed and Root Bacterization, pp. 181–197 (1974), which is incorporated herein by reference. In the aspect of the invention where peat is utilized, MKB may be cultured in fermentors to reach high population levels (i.e. $10^8$–$10^9$ cells/ml) and then added to pre-sterilized peat. The inoculum thereafter may be applied to seeds (by preparing a slurry containing the peat/bacteria mixture and gums or sugars to improve adhesion), by applying directly to soil (by dripping peat suspensions into planting furrows) or by mixing with other planting media, such as peat or saw dust (see Okon et al., CRC Crit. Rev. Biotechnology, 6:61–85 (1987), which is incorporated herein by reference).

Further, MKB may be entrapped by known methods in various biopolymers such as polyacrylamide (Dommergues et al., Appl. Environ. Microbiol., 37:779–781 (1979); xanthan gums and carob gums (Mugnier et al., Appl. Environ. Microbiol., 50:108–114 (1985)); and alginate (Bashan, Appl. Environ. Microbiol., 51:1089–1098 (1986). All of which are incorporated herein by reference.

In another aspect of the invention, MKB may used as an inoculum and applied either alone (monoculture) or in combination with other agronomically beneficial microorganisms. In a very important aspect of the invention, MKB is suspended with seeds to provide about $10^8$ to about $10^9$ cells/ml/seed. This suspension of seeds and microorganism is then planted into the soil. MKB is physiologically compatible with a wide range of bacteria and fungi, including for example, Bacillus, Pseudomonas, Rhizobia, phototrophic and cellulose degrading bacteria, Clostridium, Trichoderma, and the like.

In another aspect of the invention, MKB, either alone in monoculture or in combination with other agronomically beneficial microorganisms, may be applied to plants or soil in combination with the application of commercial fertilizer. In this aspect of the invention, inoculation with MKB is effective for increasing plant productivity over treatments where fertilizer is used without any crop inoculant.

Effect on Plant Growth and Soil Quality

In an important aspect of the invention, MKB acts to improve plant productivity and soil quality through nitrogen fixation, by improving uptake of minerals by plants, by stimulating plant growth, and by inhibiting a wide range of phytopathogenic microflora.

Nitrogen Fixation: Nitrogen fixation by MKB occurs over a wide range of environmental conditions. For example, nitrogen fixation occurs over a temperature range of from about 10° C. to about 40° C., with the optimal temperature being about 22° C. to about 30° C. In this aspect of the invention, pure cultures of MKB have a nitrogenase activity of from about 100 to about 200 micrograms $N_2$/10 ml culture/2 days. Similar levels of nitrogen fixation are observed in soil when MKB is applied to soil as a crop inoculant.

Improving mineral uptake: In another important aspect of the invention, MKB is able to produce amino acids which act to facilitate transport of nitrogen into plants. For example, MKB produces asparaginic acid and proline in levels effective for aiding the assimilation nitrogen by plants.

Stimulating plant growth: In an important aspect of the invention, MKB's ability to stimulate plant growth is attributable at least in part to its ability to produce plant growth regulators, such as indole acetic acid (IAA). In this aspect of the invention, MKB is effective for providing at least about 500 micrograms of IAA per mg of protein.

Inhibition of phytopathogenic microflora: In another important aspect of the invention, MKB is effective for inhibiting the growth of phytopathogenic microflora which commonly occur in the root zone and which tend to have a detrimental effect on plant productivity. As used herein, "inhibiting the growth of phytopathogenic microflora" refers to not only to inhibiting an increase in the biomass of the phytopathogenic microflora but also inhibiting any metabolic activities which may decrease plant productivity. Examples of phytopathic bacteria and fungi that MKB is known to inhibit the growth of include Fusarium oxysporum, Thelaviopsis basicola, Alternaria, Aspergillus flavus, Mucor fragilis, Penicillum and the like.

The following examples illustrate methods for carrying out the invention and should be understood to be illustrative of, but not limiting upon, the scope of the invention which is defined in the appended claims.

EXAMPLES

Example 1

Characteristics of MKB

MKB is an aerobic microorganism possessing a mainly respiratory metabolism with $O_2$ as a terminal electron acceptor. Additional biochemical characteristic were determined by standard methods known in the art. Additional characteristics are as follows.

| | |
|---|---|
| oxidase | + |
| catalase | + |
| Anaerobic growth with nitrate | |
| reduces $NO_3$ to $NO_2$ | + |
| reduces $NO_2$ to $N_2O$ | + |
| reduces $N_2O$ to $N_2$ | + |
| Starch hydrolysis | − |
| Urease | + |
| Liquification of gelatin | − |
| Indole formation from tryptophane | − |
| Growth in presence of 3% NaCl | − |
| Reaction of Voges-Proskauer | − |
| Reaction with Methy-Red | − |
| Growth on milk with lacmus | alkilining |
| Mol % G + C of DNA | 69% GC |
| Temperature range of nitrogen fixation and growth | 10–40° C. |
| Temperature optimum | 22–30° C. |
| pH range of nitrogen fixation and growth | 5.5–8.5 |
| pH optimum | 6.5–7.2 |

Example 2

Growth Mediums

MKB may be grown and maintained on the following mediums.

| | g/l |
|---|---|
| Semisolid Nitrogen Free Medium D | |
| sodium malate | 5.0 |
| $K_2HPO_4$ | 1.74 |
| $KH_2PO_4$ | 0.91 |
| $MgSO_4\ 7H_2O$ | 0.3 |
| $CaCl_2\ 6H_2O$ | 0.1 |
| $FeCl_2\ 6H_2O$ | 0.01 |
| agar | 4.0 |
| $H_3BO_3$ | 5.0 |
| $Na_2MoO_4\ 2H_2O$ | 5.0 |
| $MnSO_4\ 4H_2O$ | 3.0 |
| KJ | 0.5 |
| $ZnSO_4\ 7H_2O$ | 0.2 |
| $Al_2(SO_4)_3\ 12H_2O$ | 0.3 |
| pH | 6.8–7.0 |
| Semisolid Nitrogen Free Medium A | |
| $K_2HPO_4$ | 1.74 |
| $KH_2PO_4$ | 0.91 |
| $MgSO_4\ 7H_2O$ | 0.3 |
| $CaCl_2\ 6H_2O$ | 0.1 |
| $FeCl_2\ 6H_2O$ | 0.01 |
| glucose | 1.0 |
| peptone | 1.0 |
| Na lactate | 0.5 |
| Na acetate | 1.0 |
| malate or Na succinate | 0.5 |
| yeast autolysate | 0.5 |
| agar—agar | 15.0 |

Example 3

Industrial Scale Growth of MKB

Prep of Legume Extract Medium

1. Legumes (seed and/or stems, but no roots) were added to water (200 g/l) and boiled for 20 minutes.

2. Solid material were separated from the mixture (by filtration) and the following components were added.

0.5% Na-malate
0.1% $(NH_4)_2SO_4$

Culture Conditions

1. MKB was inoculated into the medium and grown with agitation and aeration at a temperature of 25° C. to 28° C. for 48 hours.

2. Cell densities reached an optical density of 3.0 to provide 600–700 mg of biomass.

Example 4

Influence of MKB Inoculation on Plant Productivity

Unless otherwise indicated, green house and field experiments were conducted by growing MKB as described and inoculating MKB at a rate of $10^8$–$10^9$ cells/ml/seed. Results were as follows.

TABLE 2

THE INFLUENCE OF INOCULATION WITH MKB ON THE CONTENT OF TOTAL NITROGEN IN PLANTS (% FROM CONTROL DATA)

|  | VARIANTS | STERILE SOIL | NON-STERILE SOIL |
|---|---|---|---|
| Rice | Control | 100 | 100 |
|  | Inoculation | 143 | 122 |
| Maize | Control | 100 | 100 |
|  | Inoculation | 150 | 113 |

TABLE 3

ASSIMILATION OF $^{15}N_2$ BY RICE PLANTS INOCULATED WITH MKB

| Rice Cultivars | Total Amount of Nitrogen Fixed by MKB (Microorganisms) | Amount of $^{15}N_2$ Assimilated by Plants | % of Total Nitrogen Assimilated |
|---|---|---|---|
| Uzros | 7.29 | 3.11 | 43.56 |
| Kuban | 8.55 | 6.56 | 76.78 |

TABLE 4

INFLUENCE OF INOCULATION WITH MKB ON THE YIELD AND NITROGEN CONTENT IN CEREALS AND GRASS UNDER GREEN HOUSE CONDITIONS (Chernozem Soil)

| CROPS | TREATMENT | WHOLE PLANT DRY WEIGHT g/% | SEEDS DRY WEIGHT g/% | % NITROGEN STEMS | ROOTS | SEEDS | CONTENT OF NITROGEN IN PLANTS mg/% |
|---|---|---|---|---|---|---|---|
| Oats | Control | 2.04/100 | 0.173/100 | 1.18 | 1.30 | 3.92 | 46.83/100 |
|  | Inoculated | 2.44/120 | 0.366/211 | 0.98 | 1.20 | 5.97 | 78.75/161 |
| Brome Smooth | Control | 1.35/100 | — | 1.63 | 1.28 | — | 21.09/100 |
|  | Inoculated | 1.68/138 | — | 1.47 | 1.20 | — | 23.67/112 |
| Fescue Meadow | Control | 1.35/100 | — | 1.59 | 1.04 | — | 20.01/100 |
|  | Inoculated | 1.58/125 | — | 1.48 | 1.04 | — | 20.83/104 |

TABLE 1

INFLUENCE OF INOCULATION WITH MKB ON THE GROWTH OF PLANTS UNDER GREEN HOUSE CONDITIONS

| Crop | Part | Control (dry weight g/pot) | Inoculated (dry weight g/pot) | Weight increase in grams | % Increase |
|---|---|---|---|---|---|
| STERILE SOIL |
| Rice | Stems | 5.6 | 7.0 | 1.4 | 25 |
|  | Roots | 2.9 | 15.9 | 13.0 | 448 |
| Maize | Stems | 24.0 | 27.0 | 3.0 | 12.5 |
|  | Roots | 28.8 | 49.6 | 20.8 | 72 |
| NON-STERILE SOIL |
| Rice | Stems | 12.4 | 13.5 | 1.1 | 9 |
|  | Roots | 3.5 | 5.1 | 1.6 | 46 |
| Maize | Stems | 18.5 | 19.8 | 1.3 | 7 |
|  | Roots | 3.7 | 5.2 | 1.5 | 40.5 |

TABLE 5

THE EFFECT OF INOCULATION OF BARLEY WITH MKB IN A PRESENCE OF DIFFERENT DOSES OF FERTILIZER (FIELD EXPERIMENT, TURF PODZOLIC SANDY LOAM SOIL)

| FERTILIZERS | VARIANTS | YIELD OF GRAIN, centner per hectare | INCREASE centner/hectare | in % |
|---|---|---|---|---|
| $P_{60}K_{90}$ | no inoculation | 27.0 | — | — |
| $P_{60}K_{90}$ | inoculation | 28.1 | 1.1 | 4.0 |
| $N_{30}P_{60}K_{90}$ | no inoculation | 38.0 | — | — |
| $N_{30}P_{60}K_{90}$ | inoculation | 43.9 | 5.9 | 15.0 |
| $N_{45}P_{60}K_{90}$ | no inoculation | 40.0 | — | — |
| $N_{45}P_{60}K_{90}$ | inoculation | 40.6 | 0.6 | 1.5 |
| $N_{60}P_{60}K_{90}$ | no inoculation | 42.7 | — | — |
| $N_{60}P_{60}K_{90}$ | inoculation | 41.9 | 0.8 | 1.8 |

TABLE 6

THE EFFECT OF INOCULATION OF WINTER WHEAT WITH MKB ON YIELD OF GRAIN AND PROTEIN CONTENT IN GRAIN (FIELD EXPERIMENT, TURF PODZOLIC SOIL)

| VARIANTS | YIELD OF GRAIN centner per hectare | INCREASE centner/ hectare | % | CONTENT OF PROTEIN IN GRAIN % | NUMBER OF STALKS | % |
|---|---|---|---|---|---|---|
| Control | 38.3 | — | — | 11.1 | 268 | 100 |
| Inoculation | 42.71 | 4.41 | 11.5 | 11.29 | 299 | 111 |

Inoculum was $10^{10}$ cells/ml and 500 grams of seed was mixed with 50 ml of suspension.

TABLE 7

THE EFFECT OF INOCULATION OF DIFFERENT GREEN CULTURES WITH MKB ON YIELD (GREEN HOUSE EXPERIMENT, SOIL AND GROUND)

| | YIELD OF PHYTOMASS, g/pot and in % VARIANTS | | | |
|---|---|---|---|---|
| | CONTROL | | INOCULATION | |
| GREEN CULTURES | (wt. in g) | % | (wt. in g) | % INCREASE |
| Lettuce | 434 | 100 | 620 | 142 |
| Fennel | 100 | 100 | 290 | 290 |
| Parsley | 185 | 100 | 220 | 120 |
| Coriander | 123 | 100 | 420 | 342 |
| Onion | 129 | 100 | 265 | 205 |

TABLE 8

EFFECT OF INOCULATION OF LEGUME PLANTS WITH MKB AND RHIZOBIA ON LEGUME AND RHIZOBIAL SYMBIOSIS (GREEN HOUSE EXPERIMENT, SAND)

| VARIANTS | Dry Wt. (g) Stems | Dry Wt. (g) Roots | Dry Wt. (g) nodules | Nitrogenase Activity (mM $C_2H_4$/hr) per g nodule | per 1 plant | CONTENT OF TOTAL NITROGEN IN PLANT (mg) |
|---|---|---|---|---|---|---|
| Rhizobium phaseoli | 5.5 | 1.5 | 0.53 | 6.2 | 1.5 | 21.1 |
| Rhizobium phaseoli + MKB | 10.8 | 2.0 | 1.40 | 9.5 | 4.0 | 30.1 |
| Bradyrhizobium japonicum | 20.5 | 15.2 | 1.60 | 5.9 | 0.6 | 23.8 |
| Bradyrhizobium japonicum + MKB | 25.7 | 18.8 | 2.20 | 11.64 | 8.38 | 33.6 |
| Rhizobium lupini | 16.39 | 8.6 | 1.13 | 1.03 | 2.0 | 97.0 |
| Rhizobium lupini + MKB | 23.6 | 15.7 | 2.2 | 3.08 | 5.76 | 146.3 |

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A biologically pure culture of *Azospirillum brasilense* SAB MKB having accession number NRRL B-30082.

2. A microbial inoculant effective for application to a plant or to soil which comprises *Azospirillum brasilense* SAB MKB.

3. A microbial inoculant according to claim 2, wherein the microbial inoculant is effective for increasing plant productivity in legumes, non-legumes and vegetable crops.

4. A microbial inoculant according to claim 2, wherein the microbial inoculant is effective for increasing plant productivity over a temperature range of from about 10° C. to about 40° C.

5. A microbial inoculant according to claim 2, wherein the microbial inoculant is effective for increasing plant productivity over a pH range of from about 5.5 to about 8.5.

6. A microbial inoculant according to claim 2, wherein the microbial inoculant further comprises agronomically beneficial stains of bacteria in addition to *Azospirillum brasilense* SAB MKB.

7. A method for improving soil quality and increasing plant productivity, the method comprising inoculating soil or plants with a microbial inoculant, wherein the microbial inoculant includes *Azospirillum brasilense* SAB MKB.

8. A method for improving soil quality and increasing plant productivity according to claim 7, herein the microbial inoculant is applied as a seed coating.

9. A method for improving soil quality and increasing plant productivity according to claim 7, wherein the microbial inoculant is applied directly to soil.

10. A method for improving soil quality and increasing plant productivity according to claim 7, wherein the microbial inoculant is applied to plants or soil as a mixture of microorganisms and planting materials.

11. A method for improving soil quality and increasing plant productivity according to claim 7, wherein the microbial inoculant further comprises agronomically beneficial stains of bacteria in addition to *Azospirillum brasilense* SAB MKB.

12. A method for improving soil quality and increasing plant productivity according to claim 7, wherein the microbial inoculant is applied to plants or soil in an amount effective for increasing the nitrogen content of the soil and plant.

13. A method for improving soil quality and increasing plant productivity according to claim 7, wherein the microbial inoculant is applied to plants or soil in combination with a commercial fertilizer.

14. A method for growing *Azospirillum brasilense* SAB MKB, the method comprising:

inoculating a legume extract medium with *Azospirillum brasilense* MKB SAB;

culturing the inoculated legume extract at a time, temperature and aeration rate effective for providing a cell density of at least about $10^8$ to about $10^9$ cells/ml.

15. A method for growing *Azospirillum brasilense* SAB MKB according to claim 14, wherein the legume extract is a water extract of legumes and includes a salt of an organic acid and a nitrogen source.

16. A biologically pure culture of *Azospirillum brasilense* SAB MKB having accession number NRRL B-30081.

* * * * *